United States Patent [19]

Grollier et al.

[11] Patent Number: 4,925,653

[45] Date of Patent: * May 15, 1990

[54] SUNSCREEN COMPOSITION CONTAINING POLYISOBUTYLENE AND ITS USE FOR THE PROTECTION OF HUMAN EPIDERMIS AGAINST ULTRAVIOLET RADIATIONS

[75] Inventors: Jean F. Grollier, Paris; Jean Cotteret, Limay, both of France

[73] Assignee: L'Oreal, Paris, France

[*] Notice: The portion of the term of this patent subsequent to May 26, 2004 has been disclaimed.

[21] Appl. No.: 294,985

[22] Filed: Jan. 6, 1989

Related U.S. Application Data

[63] Continuation of Ser. No. 931,043, Nov. 17, 1986, abandoned, which is a continuation of Ser. No. 721,673, Apr. 10, 1985, Pat. No. 4,668,505.

[30] Foreign Application Priority Data

Apr. 13, 1984 [LU] Luxembourg ............................. 85.304

[51] Int. Cl.$^5$ ........................... A61K 7/40; A61K 7/42; A61K 7/44; A61K 9/12
[52] U.S. Cl. ................. 424/47; 424/DIG. 5; 424/59; 424/60; 514/937; 514/938; 514/944
[58] Field of Search ........................ 424/59, 60, 83, 47

[56] References Cited

U.S. PATENT DOCUMENTS

| | | | |
|---|---|---|---|
| 2,312,715 | 3/1943 | Holmes et al. | 424/83 |
| 2,628,187 | 2/1953 | Frohmader et al. | 424/83 |
| 4,164,563 | 8/1979 | Chang | 424/83 |
| 4,264,581 | 4/1981 | Kerkhof | 424/60 |

FOREIGN PATENT DOCUMENTS

| | | | |
|---|---|---|---|
| 746971 | 8/1970 | Belgium | 424/83 |
| 0055857 | 7/1982 | European Pat. Off. | 424/60 |
| 2431290 | 2/1980 | France | 424/60 |

OTHER PUBLICATIONS

Sagarin, Cosmetics Science and Technology, 9/1957, pp. 199 to 201.

Primary Examiner—Dale R. Ore
Attorney, Agent, or Firm—Fleit, Jacobson, Cohn, Price, Holman & Stern

[57] ABSTRACT

The present invention relates to a sunscreen composition containing at least one oil-soluble agent absorbing UV rays as well as at least one polyisobutylene which is liquid at ambient temperature, with a viscosity-average molecular weight of between 8,000 and 65,000, in a cosmetically acceptable medium incorporating at least one fatty phase.

Such a sunscreen composition, applied to the skin, has an improved protection index.

5 Claims, No Drawings

SUNSCREEN COMPOSITION CONTAINING POLYISOBUTYLENE AND ITS USE FOR THE PROTECTION OF HUMAN EPIDERMIS AGAINST ULTRAVIOLET RADIATIONS

This application is a continuation of application Ser. No. 931,043, filed Nov. 17, 1986, which is a continuation of application Ser. No. 721,673, filed April 10, 1985, now U.S. Pat. No. 4,668,505, issued May 26, 1987 now abandoned.

The present invention relates to a sunscreen composition containing polyisobutylene the effect of which is to increase the protection index of the said screen composition in respect of ultraviolet radiations, as well as to the use of the said composition to protect human epidermis against ultraviolet radiations.

It has already been recommended to reinforce the efficiency of a UV filter in a sunscreen composition by the use of polymers which are both substantive and polar. Polar polymers are understood to be polymers which have the capacity to form polar bonds with the screening agent through the intermediacy of physical forces such as dipole-dipole, the hydrogen bond, and induced dipole-dipole. Such compositions are described in European Patent Application 55,857.

It has also been proposed to employ polyethylene of low molecular weight, between 1,100 and 2,000, in a sunscreen product, to improve the absorption properties in respect of ultraviolet radiations and to increase the protection index of the screening agent.

Such compositions are described in French Patent Application 2,431,290 and in U.S. Pat. No. 4,264,581.

However, all these compositions have disadvantages the consequence of which is not insignificant.

The polyethylene employed in the prior art is a crystalline or semicrystalline powder which has to be heated to a temperature close to its softening point (95° C.) in the fatty phase. The emulsion can only be produced by contact of this fatty phase heated to 95° C. with water heated to the same temperature. This operation represents a considerable outlay of energy and the high temperature presents a risk of degrading the UV screens having low thermal stability.

The Applicant Company has found that, by adding to a sunscreen composition containing liposoluble UV screens, a polyolefine which is liquid in the physical sense of the term, of an amorphous and nonpolar kind, such as a polyisobutylene of a molecular weight which is situated in a defined range, a sunscreen composition is obtained whose protection index is higher than that of a composition which contains only the liposoluble UV screen.

Polyisobutylene is distinguished from the polymers previously employed in sunscreen compositions by the fact that it is wholly amorphous in kind, in contrast to polyethylene which is a semicrystalline or crystalline polyolefine. It is also nonpolar with a softening point which is considerably lower than that of polyethylene, since it is liquid in the physical sense of the term at ambient temperature.

Furthermore, polyisobutylene has the property of being perfectly translucent at ambient temperature, and this property is retained in the presence of a suitable oily phase. Consequently, this offers the possibility of producing transparent compositions, which is not the case with polyethylene.

The subject of the present invention is consequently a sunscreen composition intended to be applied on human epidermis, containing at least one oil-soluble agent absorbing ultraviolet radiations and at least one polyisobutylene which is liquid at ambient temperature, with a viscosity-average molecular weight of between 8,000 and 65,000, in a cosmetically acceptable medium incorporating at least one fatty phase.

In contrast to the compositions known previously, the preparation of the compositions according to the invention does not involve large outlays of energy because it is carried out merely by mixing at a temperature relatively close to ambient temperature. It is also possible to produce, as shown above, single-phase compositions, or even transparent compositions where appropriate.

By virtue of the remarkable adhesion of polyisobutylene to skin, on the one hand, and of its property of reducing the transmission of water vapour, on the other hand, the sunscreen composition according to the invention has a better resistance to seawater and to swimming pool water as well as to perspiration relative to the compositions known previously. Moreover, it maintains the properties of the skin.

Polyisobutylene is present in the sunscreen composition according to the invention in a proportion of 1 to 20% by weight, and preferably 4 to 15% by weight, relative to the total weight of the composition.

The polyisobutylenes employed in the sunscreen composition according to the invention are viscous liquids with a viscosity-average molecular weight of between 8,000 and 65,000, which have a glass transition temperature of $-50°$ C. and are soluble in an oily phase. Use is preferably made of polyisobutylenes with a viscosity-average molecular weight of between 30,000 and 60,000 and more particularly the polyisobutylenes sold by BASF under the trade names Oppanol B 10 and Oppanol B 12, and those sold by Esso under the names Vistanex LM-MS and Vistanex LM-MH.

The sunscreen composition according to the invention contains one or more agents which absorb ultraviolet radiations of a known type and which are oil-soluble.

They are present in the composition at a total concentration of 1 to 20% by weight and, preferably, 2 to 15% of the total weight of the composition.

Among the oil-soluble UV screens which are suitable for the sunscreen composition according to the invention, mention can be made of UV screens having an absorption maximum in the wavelength region from 280 to 320 nm, that is to say in the UV-B region, such as, for example:

3-benzylidene-d,l-camphor 3-(4'-methylbenzylidene)-d,l-camphor, sold under the trade name Eusolex 6300;

para-substituted 3-benzylidenecamphors, of formula:

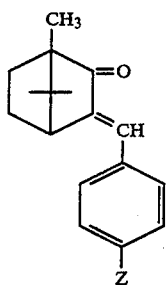

where
- Z denotes the groups —CH$_2$—I,—CH$_2$Br or —CHBr$_2$, —CH$_2$R, —CHR'R', —CHO, —COOR" with
- R=—NR$_1$R$_2$, —OR$_4$, —OCOR$_5$, —SR$_6$, —CN, —COOR",
- R$_1$ and R$_2$=H, C$_1$-C$_{18}$ alkyl, hydroxyalkyl or alternatively together with the nitrogen atom they form a hetero-cyclic ring,
- R$_4$=H, alkyl, polyoxyethylene, substituted or unsubstituted aryl, menthyl, dialkylaminoalkyl,
- R$_5$=alkyl, alkenyl, aryl, aromatic or non-aromatic heterocyclic ring containing 5 to 6 ring members,
- R$_6$=H, alkyl, aminoalkyl, hydroxyalkyl, aryl,
- R'=—OR'$_4$ or —SR'$_6$ in which R'$_4$ and R'$_6$ can have the same values respectively as R$_4$ and R$_6$ except the values hydrogen, polyoxyethylene, hydroxyalkyl, and aryl,
- R"=alkyl;

these compounds are described in French Patents 2,383,904, 2,402,647 and 2,421,878 of the Applicant Company;

esters and derivatives of p-aminobenzoic acid, such as:
ethyl p-aminobenzoate, sold under the trade name Benzocaine
isopropyl p-aminobenzoate
isobutyl p-aminobenzoate sold under the trade name Cycloform
glyceryl p-aminobenzoate, sold under the trade name Escalol 106
allantoin p-aminobenzoate, sold under the trade name Alpaba
ethyl N-ethoxy-p-aminobenzoate, sold under the name SC 9155
ethyl N-(2-hydroxypropyl)-p-aminobenzoate and ethyl N,N-bis(2-hydroxypropyl)-p-aminobenzoate, which are sold under the trade name Amerscreen P
ethyl 4-dimethylaminobenzoate
amyl 4-dimethylaminobenzoate or "Padimate" according to the common international name, sold under the trade name Escalol 506
2-ethylhexyl 4-dimethylaminobenzoate, sold under the trade name Escalol 507;
3,3,5-trimethylcyclohexyl 2-acetamidobenzoate;
anthranilates such as:
menthyl anthranilate
trimethylcyclohexyl N-acetylanthranilate;
cinnamates such as:
benzyl cinnamate
menthyl or homomenthyl cinnamate
octyl cinnamate, sold under the trade name Prosolal S 8
ethyl α-cyano-β-phenylcinnamate, sold under the trade name Uvinul N 35
2-ethylhexyl α-cyano-β-phenylcinnamate, sold under the trade name Uvinul N 539
hexyl α-cyano-β-p-methoxycinnamate
2-ethylhexyl p-methoxycinnamate, sold under the trade names Parsol MCX and Neo Heliopan AV
amyl and isoamyl p-methoxycinnamate sold under the trade name Neo Heliopan E 1000
propyl p-methoxycinnamate
cyclohexyl p-methoxycinnamate
2-ethoxyethyl p-methoxycinnamate or "Cinoxate" according to the common international name, sold under the trade name Giv-Tan F;
salicylates such as:
2-ethylhexyl salicylate
4-isopropylbenzyl salicylate
benzyl salicylate
menthyl and homomenthyl salicylates, which are sold respectively under the trade names Contrasol and Filtrasol A;
certain benzoxazole derivatives such as:
2-(p-toluene)benzoxazole
5-methyl-2-phenylbenzoxazole, sold under the trade name Witisol;
other compounds such as:
5-(3,3-dimethyl-2-norbornylidene)-3-penten-2-one, sold under the trade name Prosolal S9
ethyl urocanate
the trioleate of 3,4-dihydroxy-5-[(3,4,5-trihydroxybenzoyl)oxy]benzoic acid sold under the trade name Solprotex 1;

and new derivatives of 3-benzylidenecamphor such as the sulphonamides described and prepared in Belgian Patent 897,241 of the Applicant Company, and more particularly the compounds of Examples 1 and 3 of formulae:

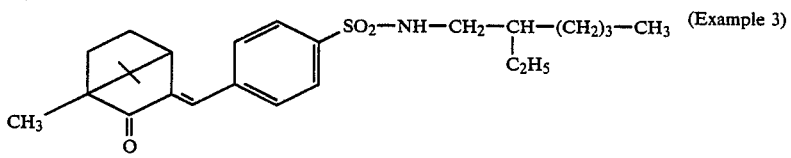

and

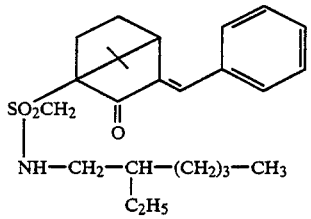

(Example 1)

as well as certain benzophenone derivatives such as:
- 2-hydroxy-4-methoxybenzophenone or "oxybenzone", sold under the trade names Spectra-Sorb UV 9, Uvinul M 40 and Eusolex 4360
- 2,2'-dihydroxy-4-methoxybenzophenone or "dioxybenzone", sold under the trade name Cyasorb UV 24
- 2,4-dihydroxybenzophenone, sold under the trade name Uvinul 400
- 2,2',4,4'-tetrahydroxybenzophenone, sold under the trade name Uvinul D 50
- 2,2'-dihydroxy-4,4'-dimethoxybenzophenone, sold under the trade name Uvinul D 49
- 2-hydroxy-4-methoxy-4'-methylbenzophenone or "mexenone" sold under the trade name Uvistat 2211
- 2-hydroxy-4-(n-octyloxy)benzophenone or "octobenzone", sold under the trade name Cyasorb UV 531
- 4-phenylbenzophenone, sold under the trade name Eusolex 3490
- 2-ethylhexyl 2-(4-phenylbenzoyl)benzoate sold under the trade name Eusolex 3573.

It is also possible to employ UV screens having an absorption maximum in the wavelength range from 320 to 400 nm, that is to say in the UV-A range, such as, for example:
- dibenzoylmethane derivatives such as:
- 4-isopropyldibenzoylmethane, sold under the trade name Eusolex 8020
- 4-tert-butyl-4'-methoxydibenzoylmethane, sold under the trade name Parsol 1789
- dianisoylmethane sold under the trade name Parsol DAM; p-benzylidenecamphor derivatives such as:
- 3-p-oxybenzylidene-2-bornanones, of formula:

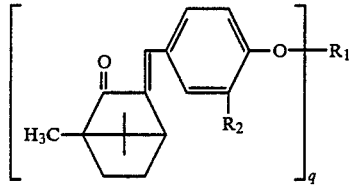

in which:

$R_1$ denotes a hydrogen atom, an optionally branched alkyl radical containing 2 to 18 carbon atoms, an alkenyl radical containing 3 to 18 carbon atoms, a radical

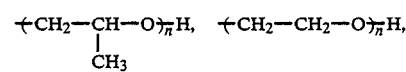

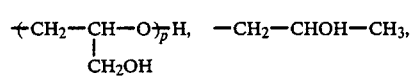

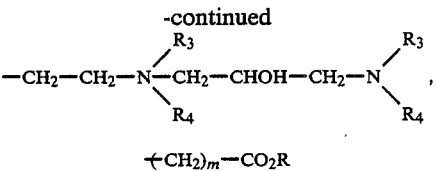

$+CH_2)_m-CO_2R$ where
- R denotes a $C_1$-$C_8$ alkyl radical or a divalent $(CH_2)_m$ or $-CH_2-CHOH-CH_2-$ radical,
- m denotes 1 to 10, n 1 to 20 and p 1 to 6;
- $R_3$ and $R_4$ each denoting a hydrogen atom or an optionally branched or hydroxylated alkyl radical or alternatively forming an aminoaliphatic heterocyclic ring with the nitrogen atom;
- $R_2$ denotes a hydrogen atom, a $C_1$-$C_4$ alkoxy radical or alternatively a divalent $-O-$ radical joined to the $R_1$ radical when the latter is also divalent;
- q denotes 1 or 2, it being understood that when q=2, $R_1$ is a divalent radical and when $R_1$=H, $R_2$ also denotes hydrogen; these compounds are described in further detail in Belgian Patent 877,596 of the Applicant Company.

1,4-dicamphomethylidenebenzenes and camphomethylidenecinnamates of formula:

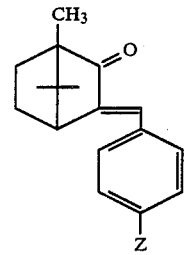

in which:

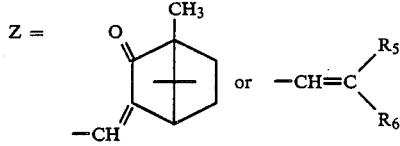

$R_5$ denotes a hydrogen atom, a $C_1$-$C_4$ alkyl group, an aryl group optionally substituted by halogen atoms or by $C_1$-$C_4$ alkoxy or alkyl groups, a $-CN$, $-COOR_7$ or

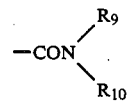

radical
$R_6$ denotes a —COOR$_8$ or

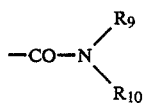

radical where $R_7$ and $R_8$ which are identical or different are alkyl, alkenyl, cycloalkyl or aralkyl radicals containing at most 20 carbon atoms, optionally substituted by hydroxy, alkoxy or amino groups, $R_9$ and $R_{10}$ which are identical or different denote a hydrogen atom or alkyl, alkenyl, cycloalkyl or aralkyl radicals containing at most 20 carbon atoms, optionally substituted by hydroxy, alkoxy or amino groups; these compounds are described in Belgian Patent 897,051 of the Applicant Company; the compound which is particularly preferred is that described in Example 7, of formula:

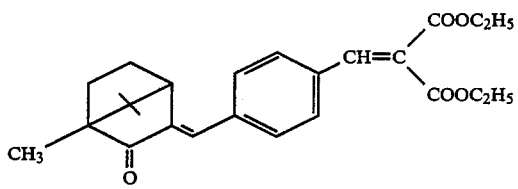

The sunscreen composition according to the invention preferably incorporates, in addition to the polyisobutylene(s) described above, at least one oil-soluble absorbing agent which absorbs in the UV-B range, responsible for erythema, that is to say in the wavelength range from 280 to 320 nm, and optionally an absorbing agent which absorbs in the UV-A range, that is to say in the wavelength range from 320 to 400 nm, or a wide-spectrum screen absorbing in UV-B and UV-A.

As wide-spectrum screens which screen in UV-A and UV-B, mention may be made of 3-cinnamylidenecamphor and certain benzotriazole derivatives such as:

2-(2'-hydroxy-5'-methylphenyl)benzotriazole sold under the trade name Tinuvin P 2-(2'-hydroxy-5'-tert-octylphenyl)benzotriazole sold under the trade name Spectra-Sorb UV 5411.

Preferably, at least one of the following compounds is employed as an absorbing agent:

2-ethylhexyl p-dimethylaminobenzoate (Escalol 507)
2-ethylhexyl p-methoxycinnamate (Parsol MCX)
3-benzylidene-d,l-camphor
3-(4'-methylbenzylidene)-d,l-camphor (Eusolex 6300)
amyl 4-dimethylaminobenzoate (Escalol 506)
homomenthyl salicylate (Filtrasol A)
2-hydroxy-4-methoxybenzophenone (Uvinul M 40 -Spectra-Sorb UV 9)
N-(2-ethylhexyl)-4-(3'-methylidenecamphor)benzenesulphonamide
N-(2-ethylhexyl)-3-benzylidene-10-camphosulphonamide optionally in combination with one of the following compounds:
tert-butyl-4-methoxy-4'-dibenzoylmethane (Parsol 1789)
4-isopropyl-dibenzoylmethane (Eusolex 8020).

The sunscreen composition according to the invention may incorporate, in addition to the polyisobutylene and the agents absorbing the ultraviolet radiations, the cosmetic adjuvants usually employed in a composition of this type.

Among the principal adjuvants which can be present in such a composition mention can be made of fatty substances such as mineral, animal or vegetable oils or waxes, fatty acids, fatty acid esters such as triglycerides of fatty acids containing from 6 to 12 carbon atoms, fatty alcohols and oxyethylenated fatty alcohols; water, monoalcohols or lower polyalcohols containing from 1 to 6 carbon atoms, or an aqueous alcohol solution.

As fatty substances, among inorganic oils, mention may be made of vaseline oil; among animal oils, whale, seal, menhaden, halibut liver, cod, tuna, turtle, tallow, neat's foot, horse's hoof, sheep's foot, mink, otter, marmot oils, and the like; among vegetable oils, almond, groundnut, wheat germ, olive, corn germ, jojoba, sesame, sunflower, palm, walnut and similar oils.

Among fatty acid esters there may be mentioned isopropyl esters of myristic, palmitic and stearic acids and fatty esters which are solid at 25° C.

As fatty substances there may also be mentioned vaseline, paraffin, lanolin, hydrogenated lanolin, acetylated lanolin and silicone oil.

Among waxes there can be mentioned Sipol wax, lanolin wax, beeswax, candelilla wax, microcrystalline wax, carnauba wax, spermaceti, cocoa butter, karite butter, silicone waxes, hydrogenated oils which are solid at 25° C., sucro-glycerides, and Ca, Mg, Zr and Al oleates, myristates, linoleates and stearates.

Among fatty alcohols there can be mentioned lauryl, cetyl, myristyl, stearyl, palmityl and oleyl alcohols, and among polyoxyethyleneated fatty alcohols, lauryl, cetyl, stearyl and oleyl alcohols containing from 2 to 20 moles of ethylene oxide.

The mono- or polyalcohols which are more particularly preferred are chosen from ethanol, isopropanol, propylene glycol, glycerol, sorbitol and aqueous alcohol mixtures are preferably mixtures of water and ethyl alcohol. The sunscreen composition according to the invention may also contain thickeners, softeners, humectants, surfactants, preservatives, antifoams, perfumes, colorants and/or pigments the function of which is to colour the composition itself or the skin, or any other ingredient usually employed in cosmetics.

The composition may be presented in various forms such as an emulsion (milk or cream), a fatty gel, a solid stick, in solution, in the form of oil or oil-alcohol lotion; the composition may be packaged as an aerosol.

When the compositions according to the invention are presented in the form of an emulsion, water-soluble screens may be added in the aqueous phase, the oily phase containing one or more oil-soluble screen(s) and the polyisobutylene.

Another subject of the invention is a process for the protection of human epidermis against UV rays, consisting in applying on the skin an effective quantity of the sunscreen composition described above.

The invention will be illustrated better with the aid of the following non-restrictive examples:

EXAMPLE 1

Sun cream

| | |
|---|---:|
| Polyisobutylene sold under the registered trade name Oppanol B 10 by BASF | 5.0 g |
| Vaseline oil | 15.0 g |
| Cetyl alcohol | 1.5 g |

-continued

| | |
|---|---|
| Mixture of cetyl stearyl alcohol (80%) and cetyl stearyl alcohol oxyethylenated with 33 moles of ethylene oxide (20%) sold under the name Sinnowax AO by Henkel | 7.0 g |
| Mixture of glycerol mono and distearates sold under the name of Geleol flakes by Gattefosse | 2.0 g |
| Glycerine | 20.0 g |
| 2-Hydroxy-4-methoxybenzophenone (Uvinul M 40 from BASF) | 1.0 g |
| 2-Ethylhexyl p-dimethylaminobenzoate (Escalol 507 from Van Dyk) | 2.5 g |
| Preservative q.s. | |
| Perfume q.s. | |
| Water q.s. | 100 g |

EXAMPLE 2

Emulsion

| | |
|---|---|
| 3-Benzylidenecamphor | 2.5 g |
| Polyisobutylene sold under the registered trade name Oppanol B 10 by BASF | 4.5 g |
| Stearic acid | 2.0 g |
| Cetyl alcohol | 1.2 g |
| Self-emulsifiable glycerol monostearate | 6.0 g |
| Sorbitan monostearate polyoxyethylenated with 60 moles of ethylene oxide | 2.0 g |
| Lanolin | 4.0 g |
| Vaseline oil | 30.0 g |
| Triethanolamine | 0.1 g |
| Perfume q.s. | |
| Preservative(s) q.s. | |
| Colorant(s) q.s. | |
| Water q.s. | 100 g |

EXAMPLE 3

Emulsion

| | |
|---|---|
| 2-Ethylhexyl paramethoxycinnamate | 3.0 g |
| Polyisobutylene sold under the name Vistanex LM-MS by Esso | 6.5 g |
| Sipol wax | 7.0 g |
| Glycerol monostearate | 2.0 g |
| Vaseline oil | 15.0 g |
| Silicone oil | 1.5 g |
| Cetyl alcohol | 1.5 g |
| Glycerine | 10.0 g |
| Perfume q.s. | |
| Preservative(s) q.s. | |
| Colorant(s) q.s. | |
| Water q.s. | 100 g |

EXAMPLE 4

Oily lotion

| | |
|---|---|
| 2-Ethylhexyl paradimethylaminobenzoate | 2.5 g |
| Polyisobutylene sold under the registered trade name Oppanol B 12 by BASF | 3.0 g |
| Vaseline oil | 64.0 g |
| Olive oil | 17.5 g |
| Sweet almond oil | 1.0 g |
| Isopropyl myristate | 12.0 g |

EXAMPLE 5

Emulsion

| | |
|---|---|
| Homomenthyl salicylate | 4.0 g |
| 4-Isopropyldibenzoylmethane | 1.0 g |
| Polyisobutylene sold under the registered trade name Oppanol B 10 by BASF | 4.0 g |
| Polyisobutylene sold under the name Vistanex LM-MH by Esso | 2.0 g |
| Vaseline oil | 10.0 g |
| Sunflower oil | 5.0 g |
| Polyoxyethyleneated hydrogenated palm oil | 5.0 g |
| Cetyl stearyl alcohol oxyethylenated with 15 moles of ethylene oxide | 5.0 g |
| Lanolin | 3.0 g |
| Propylene glycol | 5.0 g |
| Perfume q.s. | |
| Preservative(s) q.s. | |
| Colorant(s) q.s. | |
| Water q.s. | 100 g |

EXAMPLE 6

Emulsion

| | |
|---|---|
| 2-Ethylhexyl paramethoxycinnamate | 2.5 g |
| 2,4-Dihydroxybenzophenone | 1.0 g |
| Polyisobutylene sold under the registered trade name Oppanol B 10 by BASF | 3.0 g |
| Polyisobutylene sold under the registered trade name Oppanol B 12 by BASF | 1.0 g |
| Cetyl stearyl alcohol oxyethylenated with 25 moles E.O. | 5.0 g |
| Cetyl alcohol | 1.0 g |
| 2-Octyldodecanol | 15.0 g |
| Vaseline oil | 5.0 g |
| Perfume q.s. | |
| Preservative(s) q.s. | |
| Colorant(s) q.s. | |
| Water q.s. | 100 g |

EXAMPLE 7

Emulsion

| | |
|---|---|
| Glycerine | 5.0 g |
| Vaseline oil | 30.0 g |
| Sorbitan stearate | 3.0 g |
| Sorbitan stearate oxyethylenated with 20 moles of ethylene oxide | 4.0 g |
| Polyisobutylene sold under the registered trade name Oppanol B 12 by BASF | 3.0 g |
| Polyisobutylene sold under the name Vistanex LM-MS by Esso | 3.0 g |
| 3-Benzylidenecamphor | 2.5 g |
| 4-[(2-Oxo-3-bornylidene)methyl]phenyl-trimethylammonium methylsulphate | 1.0 g |
| Preservative | 0.5 g |
| Perfume q.s. | |
| Water q.s. | 100 g |

EXAMPLE 8

Oil

| | |
|---|---|
| N-(2-Ethylhexyl)-4-(3'-methylidenecamphor)-benzenesulphonamide described and prepared in Belgian Patent 897,241, Example 3 | 5 g |
| Polyisobutylene sold under the registered trade name Oppanol B 10 by BASF | 5 g |
| Vaseline oil q.s. | 100 g |

We claim:

1. In a sunscreen composition intended to be applied on human epidermis comprising 1 to 20% by weight of at least one oil-soluble agent absorbing UV-B rays selected from the group consisting of 2-ethylhexyl p-dimethylaminobenzoate, 2-ethylhexyl p-methoxycinnamate, 3-benzylidene-d,1-camphor, 3(4'-methylbenzylidene)-d,1-camphor, amyl 4-dimethylaminobenzoate, 2-ethylhexyl salicylate homomenthyl salicylate, 2-hydroxy-4-methoxybenzophenone, N-(2-ethylhexyl)-4-(3'-methylidenecamphor)benzenesulphonamide and N-(2-ethylhexyl)-3-benzylidene-10-camphosulphonamide in a cosmetically acceptable medium comprising a fatty phase, said sunscreen composition being in the form of an emulsion, a fatty gel, an oily or oil-alcohol lotion, a solid stick or an aerosol, the improvement comprising adding to said sunscreen composition 1 to 20% by weight of at least one polyisobutylene which is liquid at ambient temperature and which has a viscosity-average molecular weight of between 30,000 and 60,000 in order to increase the sun protection index of said sunscreen composition.

2. Sunscreen composition according to claim 1, and further comprising an agent absorbing UV-A rays selected from the group consisting of tert.butyl-4-methoxy-4'-dibenzoylmethane and 4-isopropyl-dibenzoylmethane.

3. Sunscreen composition according to claim 1 which contains 4 to 15% by weight of polyisobutylene.

4. Composition according to claim 1 which contains 2 to 15% by weight of at least one oil-soluble agent absorbing UV-B rays.

5. Sunscreen composition according to claim 1 which contains cosmetic adjuvants selected from the group consisting of mineral oils, animal oils, vegetable oils, mineral waxes, animal waxes, vegetable waxes, fatty acids, fatty acid esters, fatty alcohols, oxyethylenated fatty alcohols, water, lower $C_1-C_6$ monoalcohols, lower $C_1-C_6$ polyalcohols, aqueous alcoholic mixtures, thickeners, humectants, surfactants, preservatives, perfumes, colorants and pigments.

* * * * *